United States Patent [19]

Smith

[11] Patent Number: 5,118,264
[45] Date of Patent: Jun. 2, 1992

[54] PURGE FLOW CONTROL IN ROTARY BLOOD PUMPS

[75] Inventor: William A. Smith, Lyndhurst, Ohio

[73] Assignee: The Cleveland Clinic Foundation, Cleveland, Ohio

[21] Appl. No.: 463,437

[22] Filed: Jan. 11, 1990

[51] Int. Cl.$^5$ ............................................. F04B 35/04
[52] U.S. Cl. ........................ 417/423.11; 415/900; 415/110; 277/13; 277/53; 600/16; 604/151
[58] Field of Search ............... 417/423.11; 415/110, 415/171.1, 900; 277/13, 14 R, 53; 600/16; 604/151; 623/3

[56] References Cited

U.S. PATENT DOCUMENTS

| | | | |
|---|---|---|---|
| 2,441,708 | 5/1948 | Luaces et al. | |
| 3,680,976 | 8/1972 | Buse | 415/110 |
| 4,047,847 | 9/1977 | Oikawa | 417/420 |
| 4,135,253 | 1/1979 | Reich et al. | 415/900 |
| 4,521,151 | 6/1985 | Flater et al. | 415/171.1 |
| 4,526,507 | 7/1985 | Bingler | 415/171.1 |
| 4,527,947 | 7/1985 | Elliott | 415/171.1 |
| 4,589,822 | 5/1986 | Clausen et al. | |
| 4,625,712 | 12/1986 | Wampler | 415/900 |
| 4,704,121 | 11/1987 | Moise | |
| 4,854,820 | 8/1989 | Zolotar et al. | 415/171.1 |
| 4,927,407 | 5/1990 | Dorman | |

Primary Examiner—Richard A. Bertsch
Assistant Examiner—Michael I. Kocharov
Attorney, Agent, or Firm—Fay, Sharpe, Beall, Fagan, Minnich & McKee

[57] ABSTRACT

A blood pump includes a housing an inlet and outlet communicating with a pump chamber. A rotor received in the pump chamber is rotated by a drive motor. A drive shaft extending between the motor and rotor passes through a seal which is purged from the non-blood side by fluid. The fluid side of the seal contains a pumping element to modulate the fluid pressure, thereby controlling the purge fluid flow.

30 Claims, 7 Drawing Sheets

PURGE FLOW CONTROL IN ROTARY BLOOD PUMPS

BACKGROUND OF THE INVENTION

This invention pertains to the art of blood pumps and more particularly to rotary blood pumps having a purge-type seal. The invention is applicable to modulation of purge flow in rotary blood pumps and will be described with particular reference thereto. However, it will be appreciated that the invention has broader applications and may be advantageously applied in other blood pumps beyond the embodiments specifically described below wherein it is desirable to control the flow of purge fluid.

Rotary blood pumps are well known in the art as exhibited by the following U.S. Pat. Nos.:
Reich, et al.—4,135,253
Wampler—4,625,712
Moise—4,704,212

Each of these has in common that a shaft seal is purged with a fluid that flows from a non-blood side to a blood side of the seal. This use of purge fluid reduces thrombus formation and clotting at the seal interface, carries away heat, and precludes blood from entering the mechanism behind the shaft seal.

A key technical problem in the design of such purged seals is to maintain an acceptable flow rate of purge fluid through the seal. If the flow rate is too low, a mixing phenomenon can result in blood flow across the seal to the non-blood side, even as purge fluid flows in the opposite direction toward the blood side of the seal. Additionally, under low flow rates, cooling and flushing of the seal interface is poor, which can result in deposition and problems associated therewith.

On the other hand, if the flow rate is too high, a patient may encounter fluid overload problems. This is still a potential problem even if the purged fluid is biocompatible. Yet another consideration with high purge flow rates is the maintenance of an adequate supply of purge fluid.

In the patents referenced above, there is no structural arrangement to adjust the pressure or flow of purge fluid in response to changing conditions. Unless external controls are included, the blood pump is configured with either a low limit or high limit under consideration. Blood pumps designed around a low limit provide an adequate minimum flow and contemplate that an acceptable high limit will not be exceeded. Conversely, blood pumps designed toward the high limit expect that purge flow will never fall below the low limit. Clearly neither arrangement is suitable.

SUMMARY OF THE INVENTION

The present invention contemplates a new and improved purge seal control arrangement in a blood pump that modulates flow of the purge fluid.

According to the present invention, a blood pump includes a housing having a pump chamber communicating with an inlet and an outlet. A rotor or impeller is received in the pump chamber and selectively rotated by a drive shaft connected to a motor. The drive shaft passes through a seal that separates the blood in the pump chamber from a drive or motor chamber. A purge fluid flows through the seal from the drive chamber to the pump chamber. A rotodynamic or positive displacement pump is included in the fluid path from the drive chamber to the pump chamber for purposes of flow control.

According to another aspect of the invention, the flow control is defined by a rotodynamic pump that decreases the purge flow pressure behind the seal as a function of increasing revolutions per minute (rpm).

According to another aspect of the invention, the flow control includes a rotodynamic pump that increases the purge of flow pressure behind the seal as a function of increasing rpm.

According to a further aspect of the invention, a positive displacement pump is driven in common with an impeller.

A principal advantage of the invention is the ability to cause purge fluid pressure to increase or decrease to follow the pressure on the blood side of the seal.

Another advantage resides in the ability to compensate for increased frictional work and heat.

Still other advantages and benefits of the invention will become apparent to those skilled in the art upon a reading and understanding of the following detailed description.

BRIEF DESCRIPTION OF THE DRAWINGS

The invention may take physical form in certain parts and arrangements of parts, preferred embodiments of which will be described in detail in the specification and illustrated in the accompanying drawings which form a part hereof and wherein.

DETAILED DESCRIPTION OF THE PREFERRED EMBODIMENTS

Referring now to the drawings wherein the showings are for purposes of illustrating the preferred embodiments of the invention only and not for purposes of limiting same, the FIGURES show a blood pump A including a pump housing B and a drive or motor housing C. The pump housing encloses a rotary pump D that is driven by drive shaft E passing through seal F. A drive shaft E is, in turn, driven by motor G.

Figure 1:
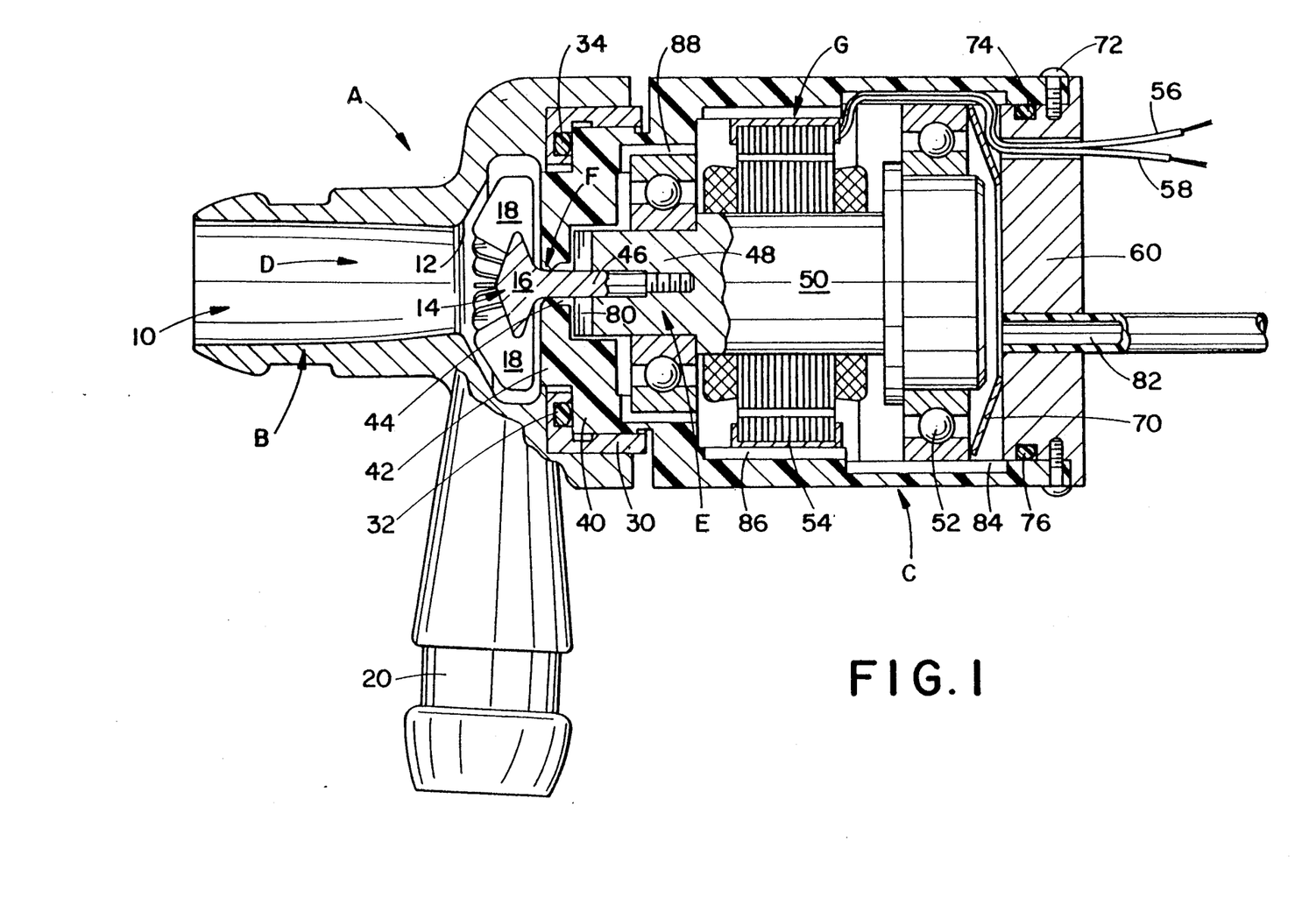
FIG. 1 is a longitudinal cross-sectional view of a blood pump according to the subject invention.

More particularly, and with reference to FIG. 1, the blood pump housing B is manufactured from a biocompatible material, or at least exteriorly coated with a biocompatible material. The pump housing includes an axial inlet 10 communicating with an enlarged diameter pump chamber 12. The pump chamber receives an impeller or pump rotor 14 that includes a central hub 16 and vanes or blades 18 extending generally radially outward from the hub. In a manner well known in the art, blood enters the pump chamber through the inlet, contacts the impeller and exits the pump chamber along a peripheral portion through tangential outlet 20. Rotation of the impeller adds energy to the blood so that the blood exits the pump chamber at a higher pressure than supplied to the inlet. Since the pumping operation of centrifugal pumps is well known, and this aspect of the subject blood pump forms no part of the invention, further discussion herein is deemed unnecessary.

It is also noted that the embodiments described and illustrated herein utilize a radial flow centrifugal pump as the preferred rotary pump. Still other rotodynamic and positive displacement pumps are contemplated without departing from the scope and intent of the subject invention. Similarly, while the motor shown is an electric type, other types of prime movers are also contemplated within the scope of the invention.

The pump housing B is secured to one end of the motor housing. Preferably a retaining collar 30 is bonded to the pump housing to provide a secure, sealed arrangement. The pump housing and collar are then secured to the motor housing. In the preferred embodiment of FIG. 1, the collar 30 includes a groove 32 adapted to receive a seal member such as O-ring 34 therein. This provides a sealed interconnection between the pump housing and one end portion 40 of the motor housing. The end portion 40 of the motor housing in the FIG. 1 embodiment also defines an end wall or rear face 42 of the pump chamber.

Extending through the end wall 42 of the pump chamber is an opening 44 adapted to receive the drive shaft E therethrough. More particularly, drive shaft E includes an impeller drive shaft portion 46 that extends through the rear face of the pump chamber and is secured to a motor drive shaft portion 48 in any well known manner. To limit passage of the blood from the pump chamber along the drive shaft, the motor housing end portion is configured to define the seal F that forms a lip seal with the impeller drive shaft portion 46. Of course still other seal arrangements than the illustrated contact type seal are contemplated and deemed to be within the scope and content of the subject invention.

According to the preferred arrangement, the motor drive shaft portion 48 is integrally formed with and axially extends from a rotor portion 50 of the motor G. As will be understood by one skilled in the art, the pump rotor 14 and rotor portion 50 of the motor comprise the rotor or entire rotating assembly of the pump. The rotor portion is preferably supported by bearing assembly 52 for rotation relative to stator portion 54 of the motor that is secured to housing C. Electrical leads 56, 58 extend through end wall 60 of the motor housing to provide power to the motor, in a manner well known in the art. Initially, a means for biasing the motor assembly such as spring 70 is interposed between the end walls 60 and the bearing assembly 52 of the motor. The end wall is selectively removable from the remainder of the motor housing through use of fasteners 72. Additionally, peripheral groove 74 is adapted to receive a seal member such as O-ring 76 so that the end wall is secured in a sealed relationship to the motor housing and opposite from the pump chamber.

As indicated above, contact type seals in blood pumps are not uncommon, nor is the combined arrangement of a contact type seal with an accompanying purge flow unknown. Contact type seals, though, are subject to wear, tolerances, and variations resulting from pressure changes. Any one of these can cause the purge fluid flow rate across the boundary between the pump chamber and the motor cavity to change. In accordance with the subject invention, the purge fluid flow is regulated to control the flow rate of purge fluid entering the pump chamber.

More particularly, and as illustrated in FIG. 1, the means for purging the sealing means includes an associated external source of biocompatible fluid. The means for regulating purge fluid flow is defined by a purge fluid pump having radially extending blades 80 defined on the motor drive shaft portion 48. A purge fluid inlet 82 is defined through end wall 60 of the motor housing to supply a biocompatible fluid to the blades 80. In the FIG. 1 arrangement, the purge fluid travels axially from the inlet 82 and around the motor through peripheral passage portions 84, 86, and 88 to reach the motor drive shaft portion adjacent the blades. Since the blades 80 rotate with the rotor portion 50 of the motor, any increase or decrease in a rotational speed of the motor results in a dynamic regulation of the purge fluid pressure through alteration of the rotational speed of the blades 80.

Purge fluid flow enters at the radial periphery of blades 80 and must flow against the pressure created by the purge fluid pump in order to pass through the lip seal and into the pump chamber. As the revolutions per minute (rpm) of the pump D increases resulting in increased flow, blood pressure at the seal F and drive shaft E interface may drop due to a variety of causes. The purge fluid pump, though, causes the purge fluid pressure at the same interface to also drop. Thus, an approximate parity of pressure differential across the lip seal is maintained over a range of operating conditions. Conversely, if pump D rpm decreases, the purge fluid pressure at the interface will increase and maintain the desired purge fluid flow, even though blood pressure at the lip seal/shaft interface may increase.

Figure 2:
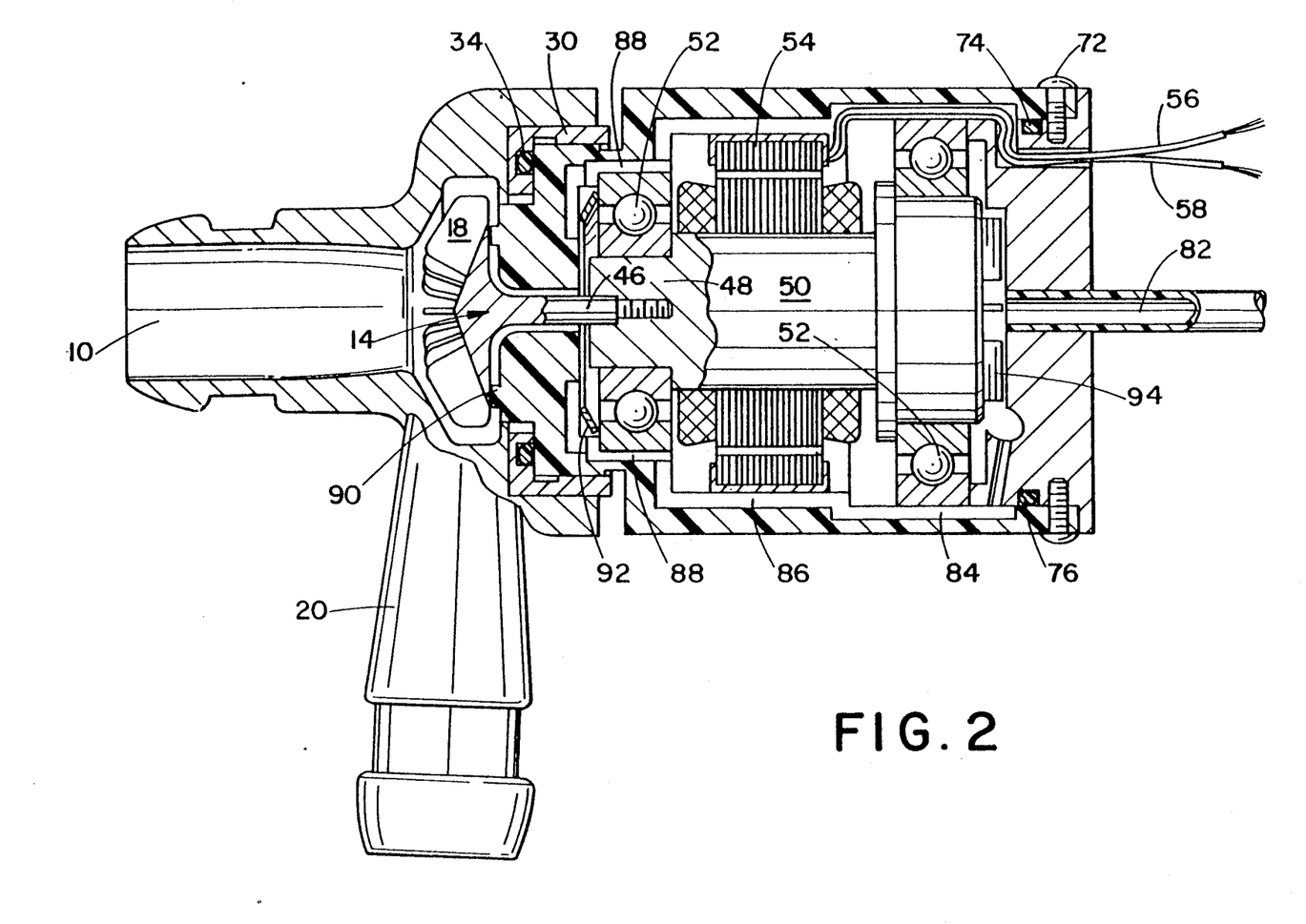
FIG. 2 is a longitudinal cross-sectional view of a blood pump illustrating a first alternative arrangement of the invention.

Referring now to FIG. 2, a modified embodiment of the blood pump, and more particularly the means for regulating purge fluid flow, will be described in detail. For ease of illustration and understanding, like numerals refer to like elements and new numerals are used to identify new elements. According to this modified arrangement, the seal F is modified so as to contact the rear face of the impeller 14 as denoted at 90. This differs from the lip seal arrangement of the FIG. 1 embodiment that defined an interface between the pump chamber and motor cavity along the drive shaft. Additionally, a means for biasing the motor in the motor housing cavity is slightly altered and is now defined by spring 92 interposed between the first end 40 of the motor housing and the bearing assembly 52. That is, the motor is urged away from the pump chamber portion or rearwardly (rightwardly) as illustrated in FIG. 2.

By disposing the face seal 90 at an intermediate or large diameter as related to the diameter of the impeller 14, it is reasonably expected that blood pressure at the seal interface will remain positive and increase with increasing pump D rpm. So that purge fluid pressure can be caused to increase with increasing pump rpm, the purge fluid pump is located at the opposite end of the motor G. Again, the purge fluid pump blades 80 are secured to the rotor portion 50 of the motor. Also in a manner similar to the FIG. embodiment, these blades 80 extend generally radially or perpendicular to the axis of rotation of the pump D. One major distinction, though, is that the purge fluid enters the blades 80 along a radially inner portion so that the purge fluid pressure can increase with increasing pump D rpm. Thus, purge fluid enters at a central portion of the radial blades 94. It will also be understood that since purge fluid pressure increases with the increasing rotational speed of the blood pump, the purge fluid pressure can also balance against increasing blood pressure at the face seal 90. An additional benefit of this arrangement is that increased purge pressure and flow results in increased cooling at a time when the seal, since operating at a higher rate, is more likely to generate increased heat.

Figure 3:
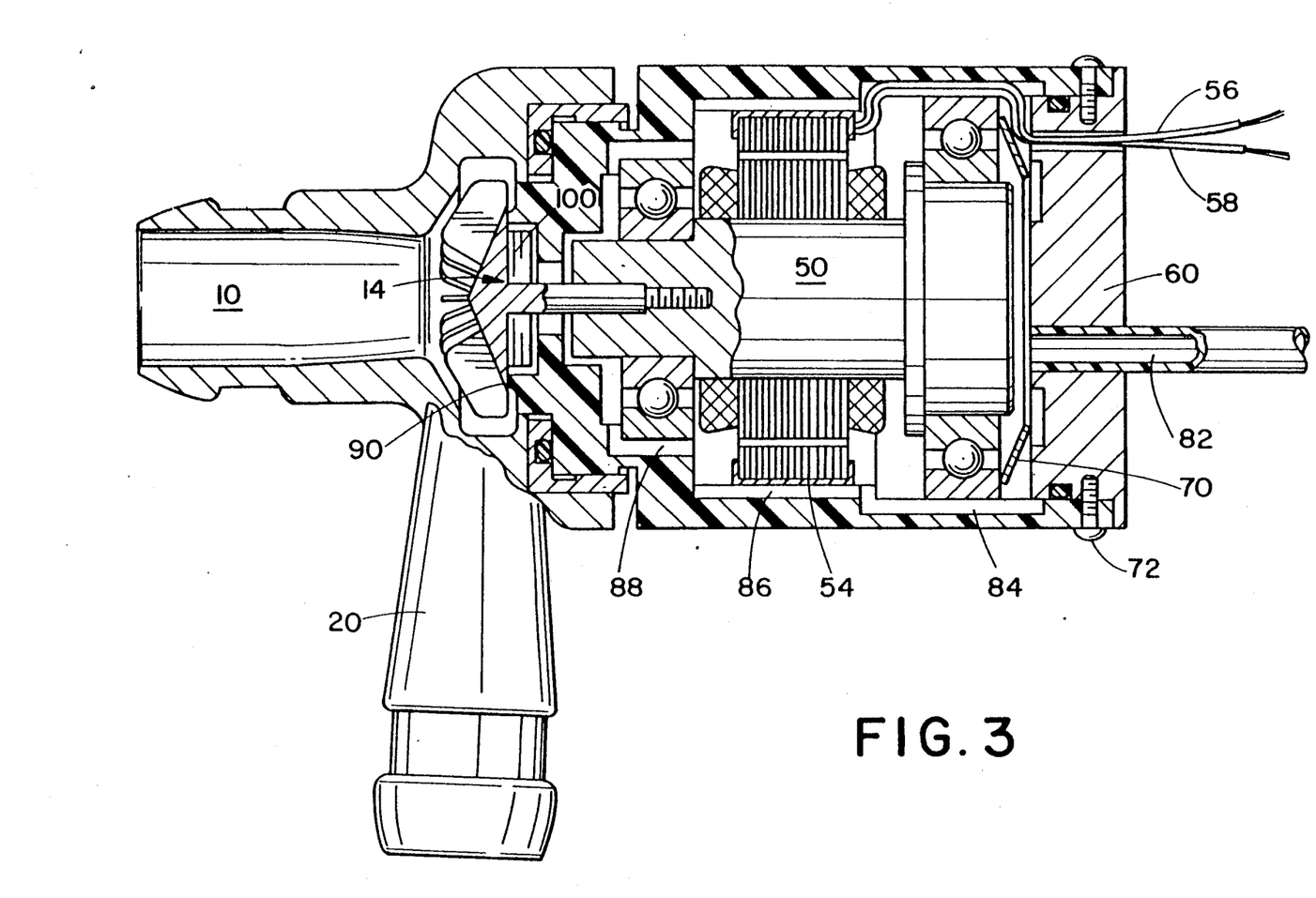
FIG. 3 is a longitudinal cross-sectional view of a blood pump showing a second alternative arrangement of the invention.

Turning now to FIG. 3, many of the concepts realized by the FIG. 2 embodiment are achieved in a slightly modified structure. Specifically, face seal 90 is still maintained at an intermediate or large diameter region along the rear face of the blood pump impeller. The biasing spring arrangement, though, of the FIG. 1 embodiment is utilized. That is, a spring 70 is interposed between the bearing assembly and end wall 60 of the motor housing. The major difference is that radially extending blades 100 are defined on the rear face of impeller 14 to regulate purge fluid flow. An opening 44 leading to the pump housing cavity is substantially enlarged so that purge fluid flow from inlet 82, along passage portions 84, 86, and 88 is adequately supplied to the blades 100 along a radially inner or central portion thereof. This assures that purge fluid pressure will correspondingly increase with increasing blood pump rpm. In all other respects, the FIG. 3 embodiment operates in substantially the same manner as the FIG. 2 embodiment.

Figure 4:
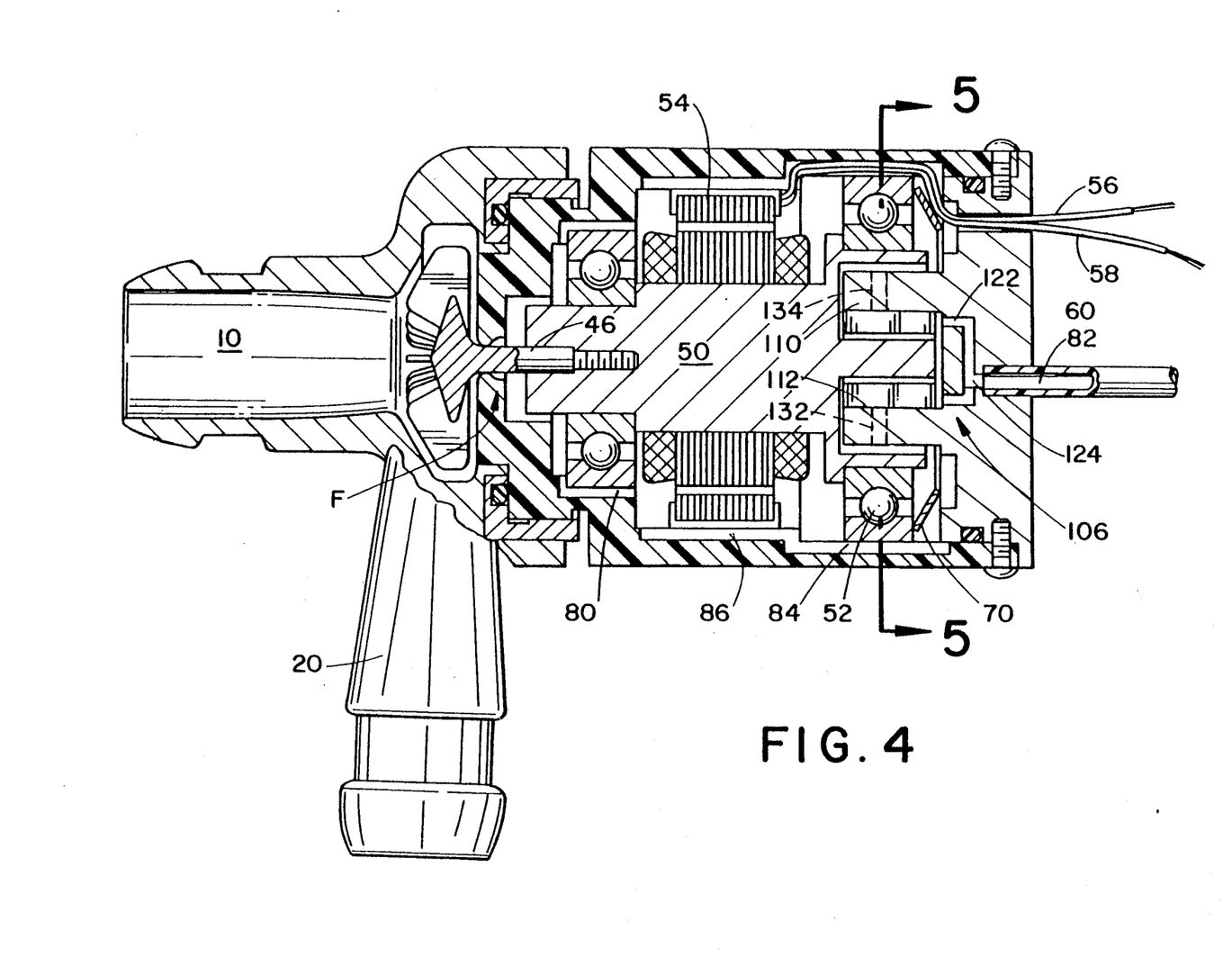
FIG. 4 is a longitudinal cross-sectional view of a blood pump showing a third alternative arrangement of the invention.
Figure 5:
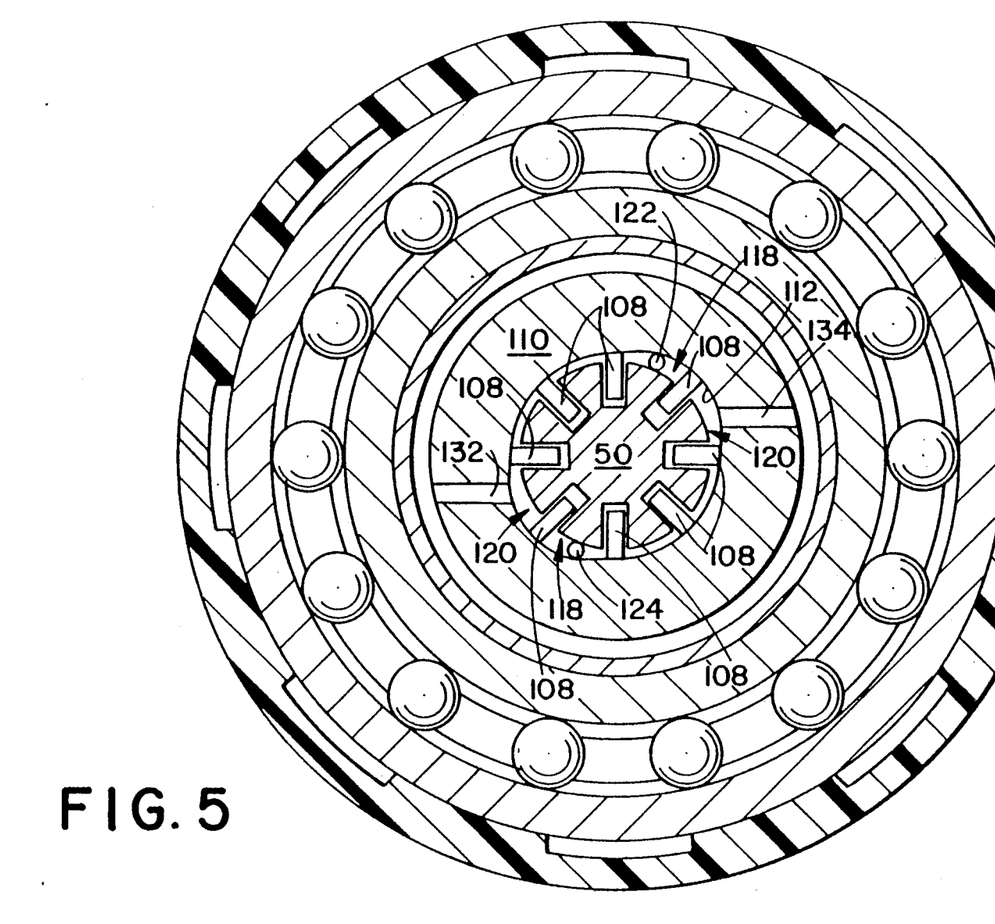
FIG. 5 is a cross-sectional view of the third alternative arrangement taken generally along the lines 5—5 of FIG. 4.

A positive displacement pump defines the purge flow pump in the modified embodiment of FIG. 4. As shown therein, the blood pump is structurally substantially the same as that of the FIG. 1 embodiment although the blades have been deleted from the motor drive shaft portion. Instead, a positive displacement pump, defined in this case by a vane pump, is utilized and disposed adjacent the inlet 82 in end wall 60. The vane pump 106 includes a series of radially extending blades 108 extending circumferentially around a rotational axis of the rotor 50. The end wall 60 is suitably modified to include an axial extension 110 that extends a longitudinal dimension of the blades. The axial extension includes an irregularly shaped recess 112 defined by inverted, mirror-imaged 180° portions. Each of these portions include an inlet region 118 that generally increases in radius, then merges into an outlet region 120 that decreases in radial dimension (FIG. 5). A purge flow inlet 82 is preferably split as shown in FIG. 4 into inlet passages 122, 124 that communicate with the recess 112 at respective inlet regions 118. The increasing radial dimension of the inlet regions permits the blades to sweep radially outwardly due to the centrifugal forces imposed by rotation of rotor 50 and sweep the purge fluid into outlet regions 120, and more specifically into outlet passages 132, 134. These outlet passages then communicate with passage portions 84, 86, 88 to provide purge fluid to the lip seal F that engages the impeller drive shaft portion 46. Since a positive displacement pump is utilized, pressure increases on the motor side of the lip seal until a gap opens at the seal interface adequate to permit purge fluid into the pump chamber.

Since the operation of a vane pump is well known in the art and individually forms no part of the subject invention, further description herein is deemed unnecessary. Likewise, other positive displacement pumps, for example a gear pump, piston pump, etc., could also be used without departing from the scope or intent of the subject invention.

Figure 6:
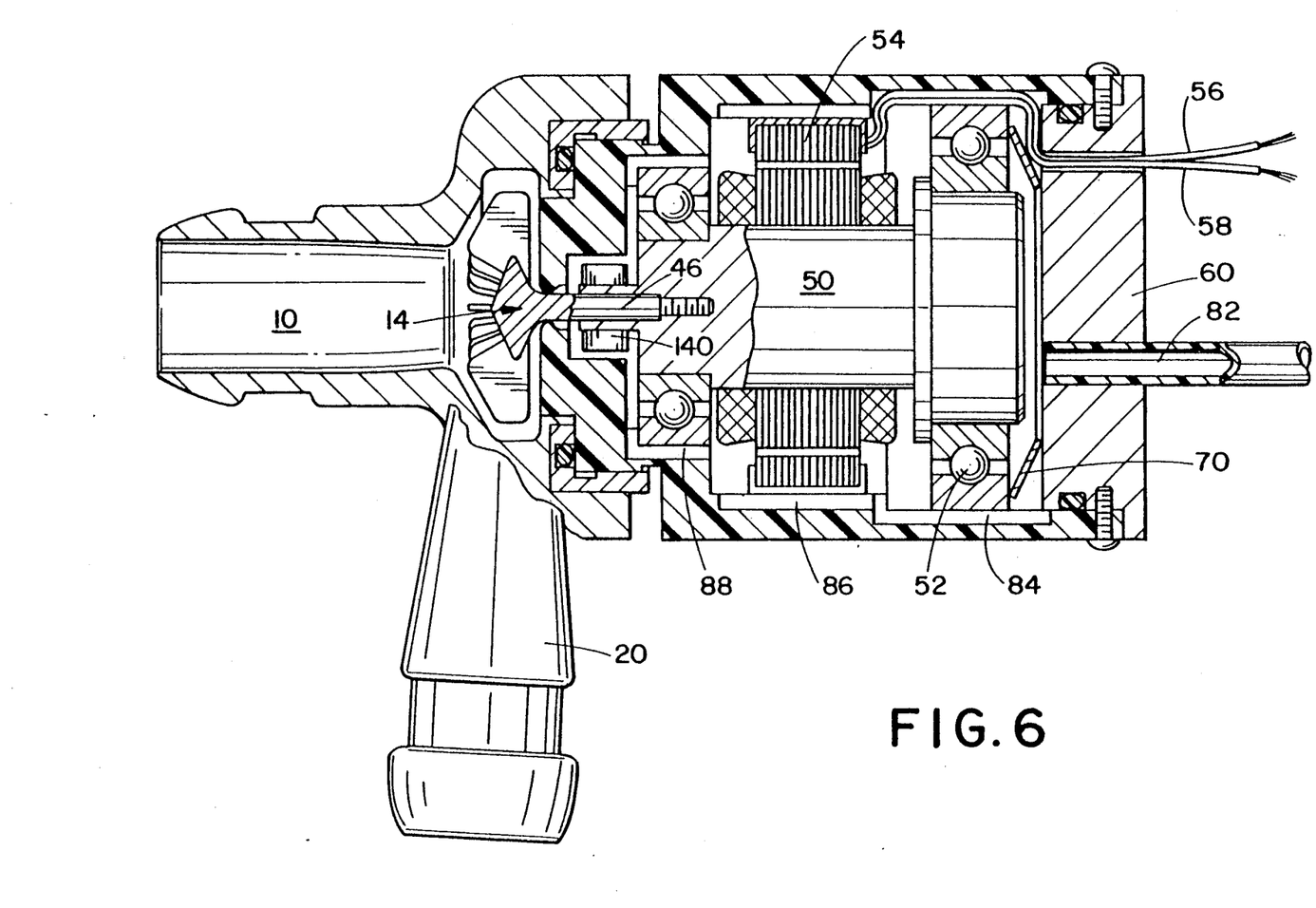
FIG. 6 is a longitudinal cross-sectional view of a fourth alternative arrangement of the invention.

The embodiment of FIG. 6 is also substantially similar to that of FIG. 1 but the blades of the purge fluid pump are disposed in a generally axial direction as opposed to the radial conformation of FIG. 1. Specifically, blades 140 are secured to the motor drive shaft portion. Purge fluid that travels from inlet 82, then along passage portions 84, 86, 88, enters the blades 140 at one end, for example the right-hand side as shown in FIG. 6. The purge fluid is then pumped through the lip seal to control potential leakage of blood into the motor housing cavity. Depending on the design of the axial blades, a purge seal pressure increase or decrease can result with an increase in blood pump rpm. This design offers the option of increasing purge fluid pressure or decreasing purge fluid pressure as a result of the parameters of the pump. In all other aspects, the FIG. 6 embodiment is structurally and functionally the same as the FIG. 1 arrangement.

Figure 7:
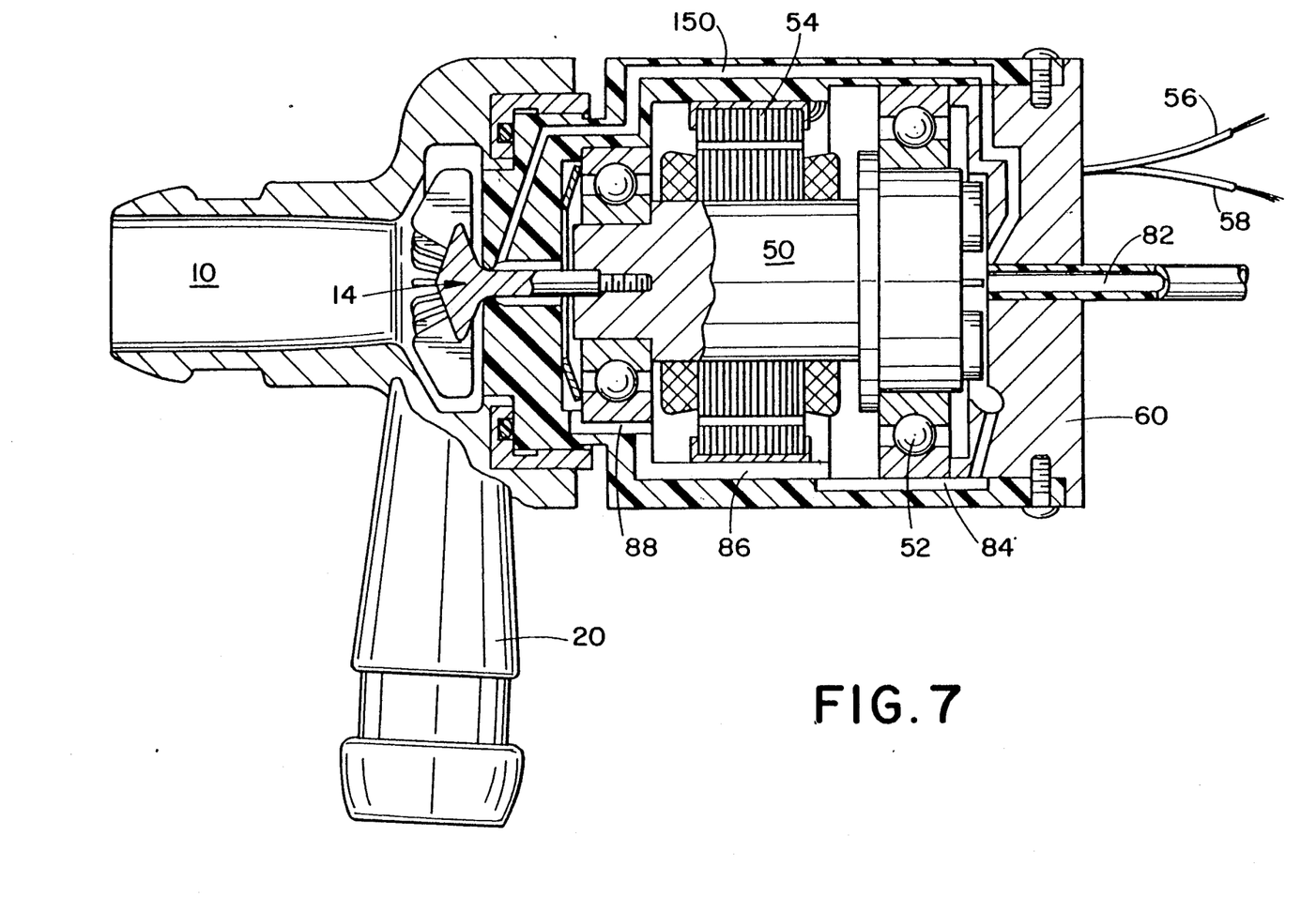
FIG. 7 is a longitudinal cross-sectional view of a fifth alternative arrangement of the invention.

Lastly, a recirculating means or regenerative arrangement for the purge fluid pump is illustrated in FIG. 7. Structurally, it is most closely associated with the embodiment of FIG. 2 where the radial blades 92 are disposed on the rear face of the rotor 50. In this arrangement, a recirculation passage 150 extends from adjacent the lip seal, through the motor housing, and re-enters the motor housing cavity adjacent purge fluid inlet 82. The primary benefit of this arrangement is the additional cooling flow that results from recirculation. Additionally, a pressure imposed at the lip seal by the purge fluid pump is dependent on the pressure/flow/rpm characteristic of the purge pump, as well as the resistance to fluid flow offered by the recirculation passage 150. As will also be apparent to one skilled in the art, the recirculate ion passage is applicable to many of the other embodiments of the blood pumps described herein.

The invention has been described with reference to the preferred embodiments. Obviously, modifications and alterations will occur to others upon the reading and understanding of the specification. It is intended to include all such modifications and alterations in so far as they come within the scope of the appended claims or the equivalents thereof.

What is claimed is:

1. A blood pump comprising:
   a housing having an inlet and outlet communicating with a pump chamber defined therein;
   a pump rotor having vanes received in the pump chamber;
   means for selectively rotating the pump rotor about a longitudinal axis;
   means for sealing the rotating means from the vanes;
   means within said housing for purging the sealing means with a supply of biocompatible purge fluid; and
   means within said housing for dynamically regulating purge fluid flow across the sealing means to control the amount of purge fluid that enters the pump chamber in response to a change in rotational speed of the pump rotor.

2. The blood pump as defined in claim 1 wherein the regulating means includes a purge fluid pump disposed on the opposite side of the sealing means from the pump chamber.

3. The blood pump as defined in claim 2 wherein the purge fluid pump is defined by a rotodynamic pump having blades extending generally radially about the longitudinal axis.

4. The blood pump as defined in claim 1 wherein the regulating means includes a rotodynamic pump having blades secured to a rear face of the pump rotor.

5. The blood pump as defined in claim 3 wherein the rotating means includes a motor having a rotor portion and a stator portion, and the blades being secured to the rotor portion of the motor.

6. The blood pump as defined in claim 5 wherein the blades are secured to the rotor portion at a region adjacent the sealing means.

7. The blood pump as defined in claim 5 wherein the blades are secured to the rotor portion at a region oppositely disposed from the sealing means such that the motor is axially interposed therebetween.

8. The blood pump as defined in claim 7 further comprising a recirculating passage extending from adjacent the sealing means to a purge fluid pump inlet to facilitate cooling of the rotating means.

9. The blood pump as defined in claim 5 wherein the blades are radially movable to facilitate pumping of the purge fluid.

10. The blood pump as defined in claim 2 wherein the purge fluid pump is a rotodynamic pump having generally axially extending blades.

11. The blood pump as defined in claim 1 wherein the regulating means includes a rotodynamic pump.

12. The blood pump as defined in claim 11 wherein the rotodynamic pump cooperates with the sealing means to increase purge fluid pressure at the sealing means with increasing rotodynamic pump rpm.

13. The blood pump as defined in claim 11 wherein the rotodynamic pump cooperates with the sealing means to decrease purge fluid pressure at the sealing means with increasing rotodynamic pump rpm.

14. The blood pump as defined in claim 1 wherein the regulating means includes a positive displacement pump.

15. The blood pump as defined in claim 14 wherein the positive displacement pump is defined by a vane pump.

16. The blood pump as defined in claim 14 wherein the positive displacement pump cooperates with the sealing means to maintain purge flow through the sealing means as a function of positive displacement pump rpm.

17. The blood pump as defined in claim 1 further comprising means for recirculating purge fluid around the rotating means to cool the blood pump during operation thereof.

18. The blood pump as defined in claim 17 wherein the regulating means controls flow through the recirculating means.

19. The blood pump as defined in claim 18 wherein the regulating means exclusively recirculates cooling flow.

20. A blood pump comprising:
a housing having an inlet and an outlet communicating with a pump chamber;
a pump rotor that rotates about a generally longitudinal axis disposed in the pump chamber and adapted to move fluid from the inlet toward the outlet;
a motor operatively coupled to the pump rotor for selectively driving the pump rotor;
a drive shaft interposed between the motor and pump rotor for transferring rotary motion of the motor to the pump rotor;
a seal defined in the housing for limiting fluid communication between the pump chamber and the motor;
means within said housing for supplying a purge flow through the seal toward the pump chamber; and
means within said housing for dynamically regulating the purge fluid flow through the seal, the regulating means including blades for modulating the purge fluid.

21. The blood pump as defined in claim 20 wherein the blades are disposed on the pump rotor at a region on the opposite side of the seal from the pump chamber.

22. The blood pump as defined in claim 21 wherein the blades are disposed generally radially around the longitudinal axis.

23. The blood pump as defined in claim 21 wherein the blades are disposed generally axially about the longitudinal axis.

24. The blood pump as defined in claim 20 wherein the regulating means includes blades disposed on a rotor portion of the motor.

25. The blood pump as defined in claim 24 wherein the blades extend generally radially about the longitudinal axis.

26. The blood pump as defined in claim 25 wherein the blades are disposed adjacent the seal.

27. The blood pump as defined in claim 25 wherein the blades are spaced from the seal at an area opposite from the motor.

28. The blood pump as defined in claim 27 wherein the blades are radially movable.

29. The blood pump as defined in claim 27 further comprising a recirculation passage that extends from adjacent the seal to the blades to facilitate cooling of the motor.

30. A blood pump comprising:
a housing having an inlet and an outlet communicating with a pump chamber;
an impeller received in the pump chamber;
a drive shaft extending from the impeller and through a pump chamber wall to a purge fluid chamber;
a motor operatively associated with the impeller through the drive shaft;
a seal interposed between the impeller and the motor;
a purge flow pump defined in the purge fluid chamber communicating with the seal for supplying an associated purge fluid thereto; and,
means within said housing operatively associated with the purge flow pump for modulating purge flow pressure in response to variations in impeller rotation.

* * * * *